US008652462B2

(12) United States Patent
Leguern

(10) Patent No.: US 8,652,462 B2
(45) Date of Patent: Feb. 18, 2014

(54) IMMUNE REGULATION

(75) Inventor: Christian A. Leguern, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 285 days.

(21) Appl. No.: 11/784,281

(22) Filed: Apr. 6, 2007

(65) Prior Publication Data

US 2008/0124348 A1    May 29, 2008

Related U.S. Application Data

(62) Division of application No. 10/503,849, filed as application No. PCT/US03/06267 on Feb. 8, 2003, now abandoned.

(60) Provisional application No. 60/361,136, filed on Mar. 1, 2002.

(51) Int. Cl.
*A01N 63/00* (2006.01)
*A61K 48/00* (2006.01)

(52) U.S. Cl.
USPC .................................. 424/93.71; 424/93.21

(58) Field of Classification Search
None
See application file for complete search history.

(56) References Cited

U.S. PATENT DOCUMENTS

| 6,455,299 B1 * | 9/2002 | Steinman et al. | 435/235.1 |
| 2002/0048564 A1 * | 4/2002 | Robbins et al. | 424/93.21 |
| 2006/0240033 A1 | 10/2006 | Tsuji | |

FOREIGN PATENT DOCUMENTS

WO    WO 9950394 A1 * 10/1999
WO    WO 02056830 A2 * 7/2002

OTHER PUBLICATIONS

Garrovillo et al., 1999, Transplantation, vol. 68: 1827-1834.*
Ali et al., 2000, Transplantation, vol. 69: 221-226.*
Pattison et al., 1997, Am. J. Med. Sci. vol. 313: 257-63.*
Garrovillo et al., 2000, Transplantation, vol. 69: S146.*
Rider et al., 1996, Mol. Immuno. vol. 22, abstract.*
Jonuleit, H. et al., "Dendritic Cells as a Tool to Induce Anergic and Regulatory T Cells", *Trends in Immunology*, vol. 22, No. 7, pp. 394-400, 2001.
Kuniyasu, Y. et al. "Naturally Anergic and Suppressive CD25+ CD4+ T cells as a Functionally and Phenotypically Distinct Immunoregulatory T Cell Subpopulation", *International Immunology*, vol. 12, No. 8, pp. 1145-1155, 2000.
Lutz, M.B. et al., "Culture of Bone Marrow Cells in GM-CSF Plus High Doses of Lipopolysaccharide Generates Excslusively Immature Dendritic Cells which Induce Alloantigen-Specific CD4 T Cell Anergy in Vitro", *Eur. J. Immunol.*, vol. 30, pp. 1048-1052, 2000.
Lutz, M.B. et al., "Immature Dendritic Cells Generated with Low Doses of GM-CSF in the Absence of IL-4 are Maturation Resistant and Prolong Allograft Survival in Vivo", *Eur. J. Immunol.*, vol. 30, pp. 1813-1822, 2000.
O'Connell, P.J. et al., "Immature and Mature CDα+ Dendritic Cells Prolong the Survival of Vascularized Heart Allografts", *The Journal of Immunology*, vol. 168, pp. 143-154, 2002.
Viret et al., "On the Self-Referential Nature of Naïve MHC Class II-Restricted T Cells", Journal of Immunology, 165:6183-6192 (2000).
Watschinger et al., "Mechanisms of Allo-Recognition", Transplantation, 57:572-576 (1994).
Xiao, B.-G. et al., "Bone Marrow-Derived Dendritic Cells from Experimental Allergic Encephalomyelitis Induce Immune Tolerance to EAE in Lewis Rats", *Clin. Exp. Immunol.*, vol. 125, pp. 300-309, 2001.
Yamazaki, S. et al., "Direct Expansion of Functional CD25+ CD4+ Regulatory T Cels by Antigen-Processing Dendritic Cells", *The Journal of Experimental Medicine*, vol. 198, No. 2, pp. 235-247, 2003.
Sayegh et al., "Induction of immunity and oral tolerance with polymorphic class II major histocompatibility complex allopepitides in the rat", PNAS, vol. 89: 7762-66 (1992).
Leguern, "Regulation of T-cell functions by MHC class II self-presentation," Trends Immunol., 24:633-638 (2003).
Rosengard et al., "The tolerant recipient: looking great in someone else's genes," J. Clin. Invest. 107:33-34 (2001).
Sayegh et al., "Induction of immunity and oral tolerance with polymorphic class II major histocompatibility complex allopepitides in the rat," Proc. Natl. Acad. Sci. USA, 89: 7762-66 (1992).
Sonntag et al, "Tolerance to solid organ transplants through transfer of MHC class II genes," J. Clin. Invest. 107:65-71 (2001).
Andersson et al., "Non-myeloablative conditioning is sufficient to allow engraftment of EGFP-expressing bone marrow and subsequent acceptance of EGFP-transgenic skin grafts in mice," Blood, 101:4305-12 (2003).
Banerjee et al., "Retrovirus-mediated transfer and expression of swine MHC class II genes in CD34+ monkey stem cells," Transplant. Proc., 28:747-748 (1996).
Baron et al., "A particular TCR beta variable region used by T cells infiltrating kidney transplants," J. Immunol., 166:2589-96 (2001).
Baron et al., "Persistence of dominant T cell clones in accepted solid organ transplants," J. Immunol., 167:4154-60 (2001).
Benichou et al., "Immunogenicity and tolerogenicity of self-major histocompatibility complex peptides," J. Exp. Med., 172:1341-46 (1990).
Blancho et al., "Molecular and cellular events implicated in local tolerance to kidney allografts in miniature swine," Transplantation, 63:26-33 (1997).
Bonasio et al., "Clonal deletion of thymocytes by circulating dendritic cells homing to the thymus," Nat. Immunol., 7:1092-1100 (2006).
Camara et al., "Human CD4+CD25+ regulatory cells have marked and sustained effects on CD8+ T cell activation," Eur. J. Immunol., 33:3473-83 (2003).
Chaturvedi et al., "A self MHC class II beta-chain peptide prevents diabetes in nonobese diabetic mice," J. Immunol., 164:6610-20 (2000).

(Continued)

*Primary Examiner* — Amy Juedes
(74) *Attorney, Agent, or Firm* — Fish & Richardson P.C.

(57) ABSTRACT

A method of regulating the immune system of a subject that involves removing antigen presenting cells from subject and loading preselected class II peptide fragments onto the subjects APC's outside the body of the subject.

30 Claims, 5 Drawing Sheets

(56) References Cited

OTHER PUBLICATIONS

Denaro et al., "Expression of xenogeneic MHC class II molecules in HLA-DR(+) and -DR(−) cells: influence of retrovirus vector design and cellular context," Xenotransplantation, 9:115-124 (2002).

Emery et al., "Bone marrow culture and transduction of stem cells in a miniature swine model," Blood Cells, 20:498-503 (1994).

Emery et al., "Expression of allogeneic class II cDNA in swine bone marrow cells transduced with a recombinant retrovirus," Transplant. Proc., 24:468-469 (1992).

Emery et al., "Expression of allogeneic class II cDNA in swine peripheral blood mononuclear cells following retroviral-mediated gene transfer into bone marrow," Transplant. Proc., 25:140-141 (1993).

Emery et al., "Expression of an allogeneic MHC DRB transgene, through retroviral transduction of bone marrow, induces specific reduction of alloreactivity," Transplantation, 64:1414-23 (1997).

Emery et al., "Retrovirus-mediated transfer and expression of an allogeneic major histocompatibility complex class II DRB cDNA in swine bone marrow cultures," Blood, 81:2460-65 (1993).

Emery et al., "Transfer of porcine MHC DRalpha into IEalpha-deficient murine bone marrow results in reduced IE-restricted Vbeta usage," Transplantation, 66:1081-88 (1998).

Ettinger et al., "A peptide binding motif for HLA-DQA1*0102/DQB1*0602, the class II MHC molecule associated with dominant protection in insulin-dependent diabetes mellitus," J. Immunol., 160:2365-73 (1998).

Fraser et al., "Specific unresponsiveness to retrovirally-transferred class I antigen is controlled through the helper pathway," J. Immunol., 154:1587-95 (1995).

Germana et al., "Retroviral vectors transfer functional MHC class II heterodimers into bone marrow: a genetic approach to tolerance induction," Transplant. Proc., 29:1129 (1997).

Gojo et al., "Xenogeneic and allogeneic skin grafting after retrovirus-mediated SLA class II DR gene transfer in baboons," Transplant. Proc., 32:289-290 (2000).

Goss et al., "Induction of extended survival of rat skin xenografts in mice by pretreatment with intrathymic xenoantigen and antilymphocyte serum," Transplantation, 54:1101-03 (1992).

Haller et al., "MHC alloantigens elicit secondary, but not primary, indirect in vitro proliferative responses," J. Immunol., 169:3613-21 (2002).

Hayashi et al., "Alloresistance to K locus class I-mismatched bone marrow engraftment is mediated entirely by CD4+ and CD8+ T cells," Bone Marrow Transplant., 18:285-292 (1996).

Hayashi et al., "Long-term engraftment of precultured post-5-fluorouracil allogeneic marrow in mice conditioned with a nonmyeloablative regimen: relevance for a gene therapy approach to tolerance induction," Transpl. Immunol., 4:86-90 (1996).

Hayashi et al., "Retroviral vectors for long-term expression of allogeneic major histocompatibility complex transduced into syngeneic bone marrow cells," Transplant. Proc., 27:178-179 (1995).

Hayashi et al., "Role of the thymus in donor specific hyporesponsiveness induced by retroviral transduction of bone marrow using an MHC class I gene," Transplant. Proc., 29:1133 (1997).

Ierino et al., "Transfer of swine major histocompatibility complex class II genes into autologous bone marrow cells of baboons for the induction of tolerance across xenogeneic barriers," Transplantation, 67:1119-28 (1999).

Khoury et al., "Acquired tolerance to experimental autoimmune encephalomyelitis by intrathymic injection of myelin basic protein or its major encephalitogenic peptide," J. Exp. Med., 178:559-566 (1993).

Leguern et al., "Expression of swine class II genes using recombinant retroviral vectors," Transplant. Proc., 23:427-428 (1991).

Leguern et al., "Intracellular MHC class II controls regulatory tolerance to allogeneic transplants," J. Immunol., 184:2394-2400 (2010).

Leguern et al., "Retrovirus-mediated transfer of MHC class II cDNA into swine bone marrow cells," J. Mol. Med., 73:269-278 (1995).

Leguern, "Potential role of major histocompatibility complex class II peptides in regulatory tolerance to vascularized grafts," Transplantation, 77:S35-S37 (2004).

Leguern, "Tolerogenic property of MHC class I and class II molecules: lessons from a gene therapy approach," Front. Biosci., 12:3133-39 (2007).

Mayfield et al., "The mechanism of specific prolongation of class I-mismatched skin grafts induced by retroviral gene therapy," Eur. J. Immunol., 27:1177-81 (1997).

Ohzato and Monaco, "Induction of specific unresponsiveness (tolerance) to skin allografts by intrathymic donor-specific splenocyte injection in antilymphocyte serum-treated mice," Transplantation, 54:1090-95 (1992).

Posselt et al., "Induction of donor-specific unresponsiveness by intrathymic islet transplantation," Science, 249:1293-95 (1990).

Saborio et al., "Regulatory T cells maintain tolerance to islet allografts induced by intrathymic injection of MHC class I allopeptides," Cell Transplant., 8:375-381 (1999).

Sachs et al., "Induction of specific tolerance to MHC-disparate allografts through genetic engineering," Exp. Nephrol., 1:128-133 (1993).

Salmon et al., "Dendritic cells enriched from swine thymus co-express CD1, CD2 and major histocompatibility complex class II and actively stimulate alloreactive T lymphocytes," Scand. J. Immunol., 52:164-172 (2000).

Sayegh et al., "Thymic recognition of class II major histocompatibility complex allopeptides induces donor-specific unresponsiveness to renal allografts," Transplantation, 56:461-465 (1993).

Shafer et al., "Expression of a swine class II gene in murine bone marrow hematopoietic cells by retroviral-mediated gene transfer," Proc. Natl. Acad. Sci. USA, 88:9760-64 (1991).

Shimada et al., "Expression of MHC class II DQ alpha/beta heterodimers from recombinant polycistronic retroviral genomes," Surg. Today, 33:183-189 (2003).

Shimada et al., "MHC class II alpha/beta heterodimeric cell surface molecules expressed from a single proviral genome," Hum. Gene Ther., 10:2397-2405 (1999).

Shimada et al., "Miniature swine MHC class II heterodimers expressed through double-copy retroviral vectors," Transplant. Proc., 28:1986-89 (1996).

Shimada et al., "Recombinant retrovirus vectors for the expression of MHC class II heterodimers," Surg. Today, 29:533-541 (1999).

Sonntag et al., "Assessment of transduction rates of porcine bone marrow," J. Hematother. Stem Cell Res., 9:721-726 (2000).

Sonntag et al., "Regulated expression of an MHC class II gene from a promoter-inducible retrovirus," Hum. Gene Ther., 11:1961-69 (2000).

Sprent and Kishimoto, "The thymus and central tolerance," Philos. Trans. R. Soc. Lond. B Biol. Sci., 356:609-616 (2001).

Vyas et al., "The known unknowns of antigen processing and presentation," Nat. Rev. Immunol., 8:607-618 (2008).

Yasumoto et al., "Mechanism of tolerance following class II gene transduction of autologous swine bone marrow," Transplant. Proc., 29:1132 (1997).

Kuniyasu, Y. et al. "Naturally anergic and suppressive CD25$^+$CD4$^+$ T cells as a functionally and phenotypically distinct immunoregulatory T cell supopulation," International Immunology, vol. 12, No. 8, pp. 1145-1155; 2000 The Japanese Society for Immunology; 11 pages.

* cited by examiner

| | | | | % Inhibition with | | | |
|---|---|---|---|---|---|---|---|
| | | | | Anti-DR | | Anti-DQ | |
| Animal # | SLA | Tg[1] | Ag tested | Direct[2] | Indirect | Direct | Indirect |
| 12426 | d | DQc | DRc, DQc | 60[3] | 57 | 50 | 60 |
| 12307 | d | DQc | DRc, DQc | 51 | ND[4] | 57 | ND |
| 11782 | c | DRd | DRd, DQd | 48 | 10 | 48 | 30 |
| Naive[5] | c | none | DRd, DQd | 60 | 60 | 30 | 70 |

FIG. 1

SEQUENCE LISTING

<160> NUMBER OF SEQ ID NOS: 9

<210> SEQ ID NO 1
<211> LENGTH: 52
<212> TYPE: PRT
<213> ORGANISM: Mus musculus

<400> SEQUENCE: 1

Gly Thr Gln Arg Ile Arg Tyr Val Thr Arg Tyr Ile Tyr Asn Arg Glu
1               5                   10                  15

Glu Tyr Val Arg Tyr Asp Ser Asp Val Gly Glu His Arg Ala Val Thr
            20                  25                  30

Glu Leu Gly Arg Pro Asp Ala Glu Tyr Trp Asn Ser Gln Pro Glu Ile
        35                  40                  45

Leu Glu Arg Ile
    50

<210> SEQ ID NO 2
<211> LENGTH: 51
<212> TYPE: PRT
<213> ORGANISM: Mus musculus

<400> SEQUENCE: 2

Gly Thr Gln Arg Ile Arg Leu Val Thr Arg Tyr Ile Tyr Asn Arg Glu
1               5                   10                  15

Glu Tyr Val Arg Tyr Asp Ser Asp Val Gly Glu Tyr Arg Ala Val Thr
            20                  25                  30

Glu Leu Gly Arg Pro Asp Ala Glu Tyr Trp Asn Ser Gln Pro Glu Ile
        35                  40                  45

Leu Glu Arg
    50

```
<210> SEQ ID NO 3
<211> LENGTH: 49
<212> TYPE: PRT
<213> ORGANISM: Mus musculus

<400> SEQUENCE: 3

Gly Thr Gln Arg Ile Arg Leu Val Ile Arg Tyr Ile Tyr Asn Arg Glu
 1               5                  10                  15

Glu Tyr Val Arg Phe Asp Ser Asp Val Glu Glu Tyr Arg Ala Val Thr
                20                  25                  30

Glu Leu Gly Arg Pro Asp Ala Glu Tyr Trp Asn Lys Gln Tyr Leu Glu
            35                  40                  45

Arg

<210> SEQ ID NO 4
<211> LENGTH: 52
<212> TYPE: PRT
<213> ORGANISM: Mus musculus

<400> SEQUENCE: 4

Gly Thr Gln Arg Val Arg Leu Leu Glu Arg Tyr Phe Tyr Asn Leu Glu
 1               5                  10                  15

Glu Asn Leu Arg Phe Asp Ser Asp Val Gly Glu Phe His Ala Val Thr
                20                  25                  30

Glu Leu Gly Arg Pro Asp Ala Glu Asn Trp Asn Ser Gln Pro Glu Phe
            35                  40                  45

Leu Glu Gln Lys
    50

<210> SEQ ID NO 5
<211> LENGTH: 52
<212> TYPE: PRT
<213> ORGANISM: Mus musculus

<400> SEQUENCE: 5

Gly Thr Gln His Val Arg Phe Leu Glu Arg Phe Ile Tyr Asn Arg Glu
 1               5                  10                  15

Glu Asn Leu Arg Phe Asp Ser Asp Val Gly Glu Tyr Arg Ala Val Thr
                20                  25                  30

Glu Leu Gly Arg Pro Asp Ala Glu Asn Trp Asn Ser Gln Pro Glu Ile
            35                  40                  45

Leu Glu Asp Ala
    50

<210> SEQ ID NO 6
<211> LENGTH: 52
<212> TYPE: PRT
<213> ORGANISM: Mus musculus

<400> SEQUENCE: 6

Gly Thr Gln Arg Val Arg Leu Leu Val Arg Tyr Phe Tyr Asn Leu Glu
 1               5                  10                  15

Glu Asn Leu Arg Phe Asp Ser Asp Val Gly Glu Phe Arg Ala Val Thr
                20                  25                  30

Glu Leu Gly Arg Pro Asp Ala Glu Asn Trp Asn Ser Gln Pro Glu Phe
            35                  40                  45

Leu Glu Gln Lys
    50
```

```
<210> SEQ ID NO 7
<211> LENGTH: 84
<212> TYPE: PRT
<213> ORGANISM: Homo sapiens

<400> SEQUENCE: 7

Gly Thr Glu Arg Val Arg Leu Leu Glu Arg Cys Ile Tyr Asn Gln Glu
 1               5                  10                  15

Glu Ser Val Arg Phe Asp Ser Asp Val Gly Glu Tyr Arg Ala Val Thr
                20                  25                  30

Glu Leu Gly Arg Pro Asp Ala Glu Tyr Trp Asn Ser Gln Lys Asp Leu
            35                  40                  45

Leu Glu Gln Arg Arg Ala Ala Val Phe Thr Asp Thr Tyr Cys Arg His
        50                  55                  60

Asn Tyr Gly Val Gly Glu Ser Phe Thr Val Gln Arg Val Glu Pro
65                  70                  75                  80

Lys Val Thr Val

<210> SEQ ID NO 8
<211> LENGTH: 81
<212> TYPE: PRT
<213> ORGANISM: Homo sapiens

<400> SEQUENCE: 8

Gly Thr Glu Arg Val Arg Phe Leu Asp Arg Tyr Phe Tyr Asn Gln Glu
 1               5                  10                  15

Glu Tyr Val Arg Phe Asp Ser Asp Val Gly Tyr Phe Ala Val Thr Glu
                20                  25                  30

Leu Gly Arg Pro Asp Ala Glu Tyr Trp Asn Ser Gln Lys Asp Leu Phe
            35                  40                  45

Glu Gln Asp Arg Ala Ala Val Val Thr Tyr Cys Arg His Asn Tyr Gly
        50                  55                  60

Val Gly Glu Ser Phe Thr Val Gln Arg Val Glu His Lys Val Thr
65                  70                  75                  80

Val

<210> SEQ ID NO 9
<211> LENGTH: 83
<212> TYPE: PRT
<213> ORGANISM: Homo sapiens

<400> SEQUENCE: 9

Gly Thr Glu Arg Val Arg Phe Leu Asp Arg Tyr Phe Tyr Asn Gln Glu
 1               5                  10                  15

Glu Ser Val Arg Phe Asp Ser Asp Val Gly Phe Thr Tyr Phe Ala Val
                20                  25                  30

Thr Glu Leu Gly Arg Pro Asp Ala Glu Tyr Trp Asn Ser Gln Lys Asp
            35                  40                  45

Leu Ile Glu Gln Arg Ala Arg Ala Val Asp Thr Tyr Cys Arg His Asn
        50                  55                  60

Tyr Gly Val Gly Glu Ser Phe Thr Val Gln Arg Arg Val Glu Gln Lys
65                  70                  75                  80

Val Thr Val
```

IMMUNE REGULATION

RELATED APPLICATIONS

This application is a divisional of U.S. patent application Ser. No. 10/503,849, with a 371(c) date of Apr. 25, 2005, which is the National Stage of PCT/US03/06267, filed Feb. 28, 2003, which claims the benefit of U.S. Provisional Patent Application Ser. No. 60/361,136, filed Mar. 1, 2012. The contents of the preceding applications are incorporated herein by reference in their entirety.

TECHNICAL FIELD

This invention relates to tissue and organ transplantation.

BACKGROUND

Since their discovery, the function of MHC class II genes has been associated with immune regulations. Although conclusions drawn from structural studies on class II heterodimers have primarily confined their role to that of presentation of antigenic peptides along with the class I molecules, numerous studies have indicated that class II proteins and/or their processed peptides should not only be regarded as histocompatibility antigens, i.e. targets of immune reactions.

The development of numerous autoimmune diseases is associated with particular class II alleles although the specific implication of these class II alleles on either the presentation of self-antigenic peptides or the progression of autoimmune diseases has not yet been established. Conversely, the description of CD4 regulatory T cells (T-reg) associated with "resistance" to insulin-dependent diabetes mellitus (IDDM) or to other autoimmune pathologies has supported the involvement of class II/CD4 interactions in peripheral suppression of anti-self reactivity. The phenomenon of T cell-mediated suppression has, likewise, specific correlates to the MHC class II region. It has been shown that partial matching for class II loci between graft donor and recipient of vascularized organs had significant beneficial effects on survival of either kidney, heart or bone marrow (BM) transplants of large species including humans.

Broadening the spectrum of potential graft donors, by using donor/recipient pairs matched for class II loci would be highly desirable in clinical transplantation, but unfortunately cannot be achieved due to the extreme structural diversity of class II molecules.

SUMMARY OF THE INVENTION

The invention provides for the modulation of the immune system, e.g., the down-regulation of T cell activation. In nature, self class II peptides, generated via the endogenous pathway of proteolysis, down-regulate T cell activation when docked onto self class II molecules at the surface of "tolerogenic" antigen presenting cell (APC), e.g., autologous BM-derived APC. The complex made of class II peptides on self class II, designated hereafter Pep2Reg (for class 2 peptide to regulate), triggers T-regulatory (T-reg) cell thymic differentiation as well as peripheral activation, resulting in the production of active T-reg which suppress potentially activated cytotoxic T cells. Methods of the invention use the formation of Pep2Reg to down regulate the immune system, e.g., the T lymphocyte pathway. This strategy for controlling, on demand, T cell reactivity, can be used in two ways: 1). Providing the correct Pep2Reg to foster the inhibition of unwanted immune responses, e.g., rejection of allo- and xenografts, autoimmune disorders including Diabetes, Rheumatoid Arthritis and Lupus, and 2). Providing a negative competitor of Pep2Reg (i.e., a compound which looks like a Pep2Reg complex but which is unable to activate T-reg) to block T-reg development and thereby allow desired T cell responses: to vaccines, cancer cells, viral infections (HIV), or any pathogen mediating a T cell response.

Accordingly, the invention features a method of regulating the immune system of a subject, e.g., a human. The method includes: providing antigen presenting cells (APC) from the subject; loading preselected class II peptide fragments onto the subjects APC's outside the body of the subject; and introducing the loaded cells into the subject, thereby regulating the immune response of the subject.

In a preferred embodiment, the method includes evaluating the extent to which the cells are loaded with the peptide.

In a preferred embodiment, the subject is a recipient of a graft from a donor. In a preferred embodiment, the method further includes introducing a graft, e.g., a vascularized graft. In a preferred embodiment, the graft is autogenic, allogenic, or xenogenic. In a preferred embodiment, the preselected class II molecule is autogenic, allogenic, or xenogenic. In a preferred embodiment, the donor and the recipient class II molecules can be matched, or partially matched.

In a preferred embodiment, the MHC class II molecule and the MHC class II peptide are synthesized in the same cell. In a preferred embodiment, the MHC class II peptide is processed by an endogenous pathway.

In a preferred embodiment, a nucleic acid encoding the class II protein to be presented as a fragment has been introduced into the APC. While not being bound by theory, it is believed that the APC's endogenously process the protein.

In a preferred embodiment, the method includes regulating T cells, e.g., recipient T regulatory T cells and/or recipient alloreactive cytotoxic T cells.

In a preferred embodiment, the thymic T regulatory T cells undergo thymic differentiation and peripheral T regulatory T cells undergo activation.

In a preferred embodiment, the alloreactive cytotoxic T cells undergo suppression.

In a preferred embodiment, the T regulatory cell population comprises CD4+CD25+ cells.

In a preferred embodiment, the method includes treating a subject: to promote graft survival; to treat a condition, disorder, or malady. The subject can have or be at risk for an autoimmune disease, e.g., an autoimmune disease selected from the group consisting of rheumatoid arthritis, diabetes mellitus, multiple sclerosis, and lupus erythematosus.

In preferred embodiment, the method includes suppressing alloreactive T cells in a subject by administering donor MHC class II molecules to the subject wherein the donor MHC class II are processed to regulate T regulatory cells.

In a preferred embodiment, an MHC class II molecule is administered: orally; intravenously; by introducing MHC class II molecules into syngeneic cells, into APC's, or administering donor-type class II+lymphocytes.

In a preferred embodiment, the method includes administering the peptide or protein to a subset of APC's. In a preferred embodiment, the subject APC's are dendritic cells, preferably immature dendritic cells, e.g., immature dendritic cells from bone marrow.

In another aspect, the invention features a purified preparation of APC's having a Pep2Reg complex, e.g., as made by a method herein described.

In another aspect, the invention features a preparation of APC's having exogenously added peptides which bind a membrane associated class II heterodimer and form a Pep2Reg complex.

In another aspect, the invention features a method of up-regulating the immune system of a subject, e.g., a human. The method includes: providing a negative competitor of Pep2Reg (i.e., a compound which mimics a Pep2Reg complex but which is unable to activate T-reg) to block T-reg development and thereby allow desired T cell responses.

In a preferred embodiment the competitor is a class 2 molecule which up regulates the response to a vaccine, cancer cells, viral infections (HIV), or any pathogen mediating a T cell response providing antigen presenting cells (APC) from the subject. "Immune system", as used herein, refers to the protective measures developed by vertebrates directed towards invading microorganisms. The system works in two different ways, by cellular immunity and by humoral immunity. The term cellular immunity means that intact cells are responsible for recognizing an invading material. Humoral immunity is based upon soluble molecules or immunoglobulins recognizing foreign material.

"Subject," as used herein, refers to any vertebrate, preferably a human.

"Antigen presenting cells," as used herein, refers to a cell which carries antigen in a form that can stimulate lymphocytes. Macrophage and dendritic cells are the most common APC's. Purified preparations of APC's or preparations, such as bone marrow, which include other cell types, can be used in methods of the invention.

"Dendritic cells," as used herein, refers to a family of professional antigen presenting cells that are present in trace amounts in virtually all organs. The major function dendritic cells is to process and present various types of antigen and various subpopulations have been identified (e.g., lymphoid, myeloid, splenic, or epidermal). A general property of all subtypes of dendritic cells seems to be that they pass through several levels of maturation during their life-span. There is evidence that certain subpopulations are able to down regulate immune responses.

"Immature dendritic cells", as used herein, refers to resting dendritic cells that are CD4+, are antigen-nonspecific, and induce T regulatory cells. "Loaded recipient antigen presenting cell (LRAPC)," as used herein, refers to APC's from a subject which presents selected peptides. A selected peptide is one which will modulate the immune response of the recipient, e.g., increased proliferation of T-reg's or donor graft acceptance.

"Immune response," as used herein, refers to the action of a subject's immune system to remove foreign matter that involves the coordinated efforts of several types of white blood cells.

"Solid organs," as used herein, refers to, for example, skin, liver, kidney, heart, eye, pancreas and lung.

"Loading", as used herein, refers to providing cell surface presentation of donor class II peptides which are endogenously processed or which are the same, substantially the same or similar as endogenously processed peptides with recipient class II membrane associated heterodimer.

"Discordant species combination", as used herein, refers to two species in which hyperacute rejection occurs when a graft is grafted from one to the other. Generally, discordant species are from different orders, while non-discordant species are from the same order. For example, rats and mice are non-discordant concordant species. Concordant species combinations do not exhibit hyperacute rejection.

"Graft", as used herein, refers to a body part, organ, tissue, or cells. Organs such as liver, kidney, heart or lung, or other body parts, such as bone or skeletal matrix, tissue, such as skin, intestines, endocrine glands, or progenitor LRAPC's of various types, are all examples of grafts. The transplant can be selected from a variety of skin grafts, fasciocutaneous grafts, musculocutaneous grafts, muscle flaps with applied skin grafts and whole organ transplants, or hematopoietic cells or tissues, e.g., from bone marrow or peripheral blood are preferred examples of a graft.

"Vascularized graft", as used herein, refers to tissue that is moved to a new location along with its own inherent blood supply.

"Help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in graft acceptance. The help reducing agent should be administered in the absence of treatments which promote cytokine, e.g., IL-2, release. Putative help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a class II matched class I and minor antigen mismatched donor monkey into the recipient. Graft acceptance to the donor kidney (as indicated by prolonged acceptance of the graft) is indicative that the putative agent is, at the dosage tested, a help reducing agent.

"Help reduction", as used herein, means the reduction of T cell help by the inhibition of the release of at least one cytokine, e.g., any of IL-2, IL-4, IL-6, gamma interferon, or TNF, from T cells of the recipient at the time of the first exposure to an antigen to which graft acceptance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing graft acceptance.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. MHC antigens in swine, e.g., miniature swine, include the products (and fragments and analogs thereof) of the SLA genes, e.g., the DRB gene.

"Miniature swine", as used herein, refers to a wholly or partially inbred pig.

"Stromal tissue", as used herein, refers to the supporting tissue or matrix of an organ, as distinguished from its functional elements or parenchyma.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient.

"Short course of an immunosuppressive agent", as used herein, means a transitory non-chronic course of treatment. The treatment should begin before or at about the time the treatment to induce graft acceptance is begun, e.g., at about the time, xenogeneic, allogeneic, genetically engineered syngeneic, or genetically engineered autologous LRAPC's are introduced into the recipient. e.g., the short course can begin on the day the treatment to induce graft acceptance is begun, e.g., on the day, xenogeneic, allogeneic, genetically engineered syngeneic, or genetically engineered autologous LRAPC's are introduced into the recipient or the short course can begin within 1, 2, 4, 6, 8, or 10 days before or after the treatment to induce graft acceptance is begun, e.g., within 1, 2, 4, 6, 8, or 10 days before or after xenogeneic, allogeneic, genetically engineered syngeneic, or genetically engineered autologous LRAPC's are introduced into the recipient. The short course can last for: a period equal to or less than about 8-12 days, preferably about 10 days, or a time which is approximately equal to or is less than two, three, four, five, or ten times the 8-12 or 10 day period. Optimally, the short course lasts about 30 days. The dosage should be sufficient to maintain a blood level sufficient to inactivate thymic or lymph node T cells. A dosage of approximately 15 mg/kg/day has been found to be effective in primates.

"Graft acceptance", as used herein, refers to an inhibition of a graft recipient's immune response which would otherwise occur, e.g., in response to the introduction of a nonself MHC antigen into the recipient. Graft acceptance can involve humoral, cellular, or both humoral and cellular responses. Graft acceptance, as used herein, refers not only to complete immunologic graft acceptance to an antigen, but to partial immunologic graft acceptance, i.e., a degree of graft acceptance to an antigen which is greater than what would be seen if a method of the invention were not employed. Graft acceptance, as used herein, refers to a donor antigen-specific inhibition of the immune system as opposed to the broad spectrum inhibition of the immune system seen with immunosuppressants.

"Suppression", as used herein, refers to the induction of T cell unresponsiveness.

"Endogenous pathway", as used herein, refers to the proteolytic processing pathway used by a cell with proteins synthesized endogenously within the cell. This proteolytic pathway results in a distinct group of peptide sequences relative to the relative to the sequences generated by endocytosis.

"Pep2Reg", as used herein, refers to the immune complex made of class II peptides presented by membrane associated self class II molecules.

"T regulatory (T-reg) cell", as used herein, refers to a subset of T cells that have been shown to inhibit pathology-inducing immune responses in a large number of models of autoimmunity and transplantation. T-reg cells can be CD4+CD25+.

"Autogenic", as used herein, refers to an identical genetic background.

"Allogeneic", as used herein, refers to having a genetic dissimilarity within the same species.

"Xenogenic", as used herein, refers to crossing a species barrier.

"Thymic differentiation", as used herein, refers to the development of specialized T cells in the thymus.

"Cytotoxic T cells", as used herein, refers to cells that kill target cells bearing appropriate antigen within the groove of an MHC class I molecule that is identical to that of the T cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

BRIEF DESCRIPTION OF THE DRAWINGS

FIG. 1 is a table showing antibody-mediated inhibition of proliferation of T cells from class II-engineered animals. [1]Class II transgene introduced. [2]The direct pathway of antigen presentation was assessed with purified T cells from class II engineered animals tested against donor-type irradiated PBLs. The indirect pathway was tested on recipient T cells, supplemented with self APC and stimulated by donor-type irradiated T cells. [3]The combination of anti-R and -DQ mAbs resulted in 90-100% inhibition in all cases. [4]Not detected. [5]Results from a naïve animal representative of 5 experiments.

DETAILED DESCRIPTION

Figure 2:
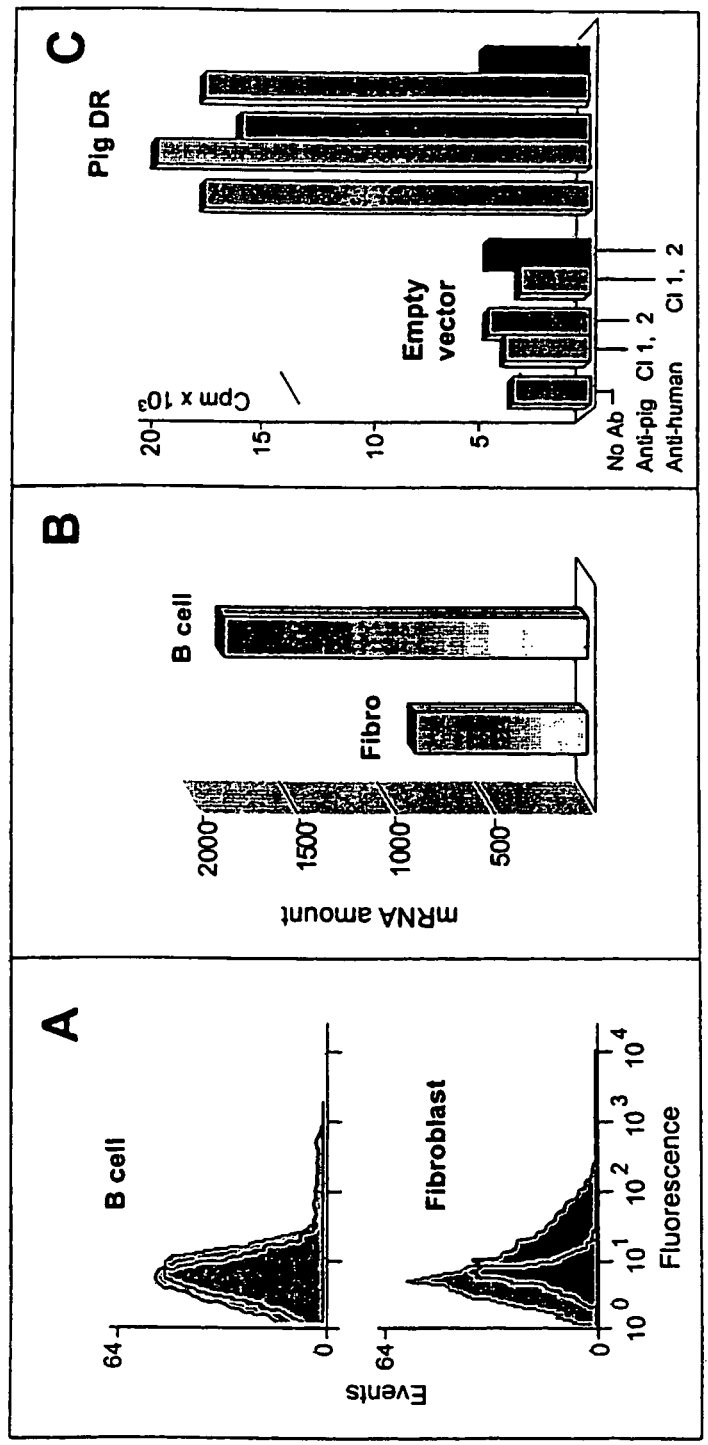
FIGS. 2A-C are graphs showing the expression of transduced MHC class II cDNAs in class II-committed cells. (A). Flow cytometry analysis of EBV-transformed human B cells from donor H65 (top) and human fibroblast line 637B both transduced with a pig DRAd and DRBd+neoR retrovirus. Surface expression of class II heterodimers was monitored by flow cytometry on neomycin-resistant transduced cells with anti-pig DR (orange), which is not cross-reacting on human DR, as well as immunoglobulin isotype control (blue) mAbs. (B). One B cell and Fibroblast clone ($2\times10^6$ cells), containing each approximately 1 viral copy per genome/cell, were analyzed for viral transcript content by Northern blot analysis of purified total RNA and hybridization with a retroviral DRB radioactive probe. Resulting radioactive signals, corresponding to the expected size band for the viral transcript on the gel, were scanned on a computer-assisted densitometer. The overall DRB signal intensities obtained were corrected for gel loading errors by standardization to the internal signal of the glyceraldehyde dehydrogenase (GAPDH) ubiquitous transcript. Corrected signal intensities for the human fibroblast (Fibro) and B cell clones were expressed in arbitrary units (mRNA amount) and were plotted. (C). Antibody blocking of T cell proliferation to transduced pig class II. H65 enriched T cells ($1\times10^6$/ml), from the B cell donor, were primed in vitro for 2×10 days with irradiated pig lymphocytes of the SLAd type ($0.5\times10^6$/ml)+human interleukin-2 (10 U/ml). Anti-pig primed H65 cells ($2.5\times10^4$ T cells/well) were cultured in triplicate in a 96 well plate (Costar Corp., Cambridge, Mass.) with $1.25 \times 10^5$/well irradiated H65 B cells infected with either the DRd vector (pig DR) or an empty vector containing only the NeoR gene. (Empty vector). H65 T cell proliferation in response to these two stimulators was measured by 3H-thymidine incorporation in replicating DNA over an 18 hour period (green bars). The influence of surface MHC class I and class II molecules, of porcine and human origin, on human T cell proliferation was measured by incorporating saturating doses of specific monoclonal antibodies during the proliferation assay (anti-pig, anti-human Cl I and II, respectively).

Methods described herein provide for regulating the T lymphocyte immune response of a subject by down regulating cytotoxic T cell activation by "class II matching" and provision of Pep2Reg complexes in transplantation of vascularized grafts and organ transplants. Methods described herein promote survival of the donor graft and decrease or eliminate the need for sustained immunosuppression.

Modulation by Pep2Reg

Nucleic acids encoding the α, the β, or the α/β chains of the class II molecule of the donor tissue are expressed in a recipient APC. This complex is referred to as Pep2Reg. Pep2Reg complexes can be provided in a number of ways. The recipient APC's can be isolated from the recipient subject with or without subsequent and culture in vitro. The Pep2Reg can be formed by introducing donor class II nucleic acid (cloned into an expression vector) into the recipient cell. The donor class II protein can be processed by an endogenous proteolytic pathway in the recipient APC, producing peptide sequences distinct from those generated through of the exogenous class II chains. The class II peptides can be presented on the surface of the recipient APC by binding to membrane-anchored class II heterodimers endogenous to the recipient APC. Pep2Reg complexes can also be obtained by "feeding" the appropriate peptide to an APC. Appropriate peptides are those which are the same or substantially the same produced by endogenous processing of class II molecules. Thus, e.g., if it is known that a certain peptide is produced by endogenous processing, it can be synthesized and supplied.

As mentioned above, the immune-complex generated by binding of the class II peptide to the class II heterodimer is designated the Pep2Reg complex and a cell having the complex on its surface is designated as a loaded recipient antigen presenting cell (LRAPC). The LRAPC's expressing the Pep2Reg are reintroduced into the subject, for example, by intravenous injection. While not wishing to be bound by theory, it is believed the cells migrate into the thymus thereby triggering thymic differentiation of T regulatory cells.

Suitable APC's for loading include professional APC's, particularly dendritic APC's. Immature dendritic APC's are much preferred. Dendritic cells can be isolated and cultured in vitro. The population of immature dendritic cells can be expanded by exposing the cultured cells to low doses of granulocyte-macrophage colony stimulating factor (GM-CSF) and interleukin-4 (IL-4) using standard technology as seen in; Jonuleit, H., E. et al. (2000) *J Exp Med.* 192:1213; Lechler, R., W. et al. (2001) *Immunity* 14:357; and O'Connell, P. J. et al. (2002) *J Immunol.* 168:143. These articles are herein incorporated by reference. The dendritic cell can be from any tissue or organ of the recipient, e.g., bone marrow, liver, spleen. Bone marrow derived immature dendritic cells is much preferred.

Grafts

Methods of the invention are useful for promoting acceptance of grafts. While not wishing to be bound by theory, it is believed that the method provides permanent or extended immunosuppression towards the transplanted graft. The grafts can supply a biological or physiological function or product. It can replace diseased, dysfunctional or absent (e.g. by surgical removal) recipient tissue. The graft can be autogenic, allogenic, or xenogenic and therefore the class II peptide can be autogenic, allogenic, or xenogenic. If xenogenic, it can be discordant or concordant. The donor graft can be any organ, tissue or cell, e.g., heart, liver, spleen, pancreas, lung, kidney, skin, hematopoietic tissue, e.g. bone marrow, hematopoietic cells or peripheral hematopoietic cells. It is preferred that the graft is vascularized.

The recipient mammal can be, by way of example, a human. The donor mammal can be, by way of example, a human or swine, e.g., a miniature swine or a nonhuman primate. Cells from the graft, or "passenger" cells within the graft (i.e: Blood cells in the circulation), preferably expresses a major histocompatibility complex (MHC) molecule or derived peptides, preferably from a class II antigen.

Methods of Loading of Class II Peptides onto Class II Molecules

The genes for donor class II heterodimers can be transcribed but not expressed as a heterodimer on the surface of class II(+) recipient cells (Example 2.). However, donor class II heterodimers can be expressed on the surface of recipient class II(−) cells.

Another embodiment of the method is that only a single chain of the donor class II heterodimer can be presented by the recipient APC which confers tolerance.

A preferred embodiment is that the Pep2Reg is a natural complex on the surface of APC's. This complex constitutes class II peptide motifs docking onto a class II heterodimer cleft (Example 3). The naturally occurring complex can account for up to 12% of the loaded class II molecules on a given APC.

Another embodiment is to use the recipient's BM-derived dendritic cells as the APC for loading the donor class II nucleic acid. Preferably, the dendritic cells are a subset of dendritic cells, e.g., immature dendritic cells, defined as class II$^+$ cells which cannot stimulate an alloresponse (Example 4 and 5). Dendritic cells are isolated and immature dendritic cells are cultured by standard techniques as previously discussed.

A preferred embodiment of the invention is that at least one subset of cells that differentiate in response to the Pep2Reg signal are T-reg cells. T-reg cells are a subpopulation of 5-10% of all peripheral CD4+ cells, as characterized in the murine system. (Example 4 and 5). These cells are identified by the cell surface markers CD4+CD25+. The main function of these cells is to suppress pathological autoaggressive T-cell responses.

Peptides can be loaded onto an APC by providing APC's into which has been inserted DNA encoding the donor's class II nucleic acid. The donor peptide is endogenously processed and then loaded. Transfection techniques include, e.g., electroporation and protoplast fusion, and recombinant retroviruses include, e.g., Moloney murine leukemia virus—as well as lentivirus-based vectors.

Peptides can also be loaded when the donor class II molecule is synthesized in the same recipient cell as is the recipient class II molecule. The donor class II molecule is proteolyzed into peptides by an endogenous proteolytic pathway of the recipient cells. The peptides are then specifically bound in the recipient class II heterodimer protein cleft on the surface of the recipient cell.

Another embodiment of the method provides loading of the donor class II peptides onto the surface of the recipient cell and accessing the amount of loading on the cell surface. Accessing the amount of loading on the surface of the APC is standard technology, as seen in: Buus, S., S. et al. (1986) *Proc Natl Acad Sci USA* 83:3968; Babbitt, B. P., et al. (1985) *Nature* 317:359; and Shimonkevitz, R., S. et al. (1984) *J Immunol* 133:2067. These articles are herein incorporated by reference.

Identification of Suitable Peptides

Polymorphic regions of donor class II are particularly suitable for forming peptides for the Pep2Reg complex. Suitable peptides for loading into the class II groove are usually between 15-25 amino acid long. Peptides of expected size derived from class II sequences, conserved and polymorphic between various individuals, can be identified from sequence databases and can be tested to determine of it is suitable for loading it onto an APC to form a Pep2Reg complex. The formation of the Pep2Reg can then be tested in vitro to determine if it down regulates T cell reactivity, e.g., to see if it activates T-reg cells which then block T cell reaction. Activation of T-reg cells by the synthetic Pep2Reg is monitored by the apparition of activation markers on Treg such as CTLA4. Emergence of T-reg is characterized by their CD4+, CD25+ phenotype. Suppression of proliferation of normal, activated T cells (CD4+, CD25neg) by T-reg is measured by coculture of these 2 cell types in presence of 3H thymidine to assess DNA replication (ie: cell division, only the normal T cells can divide, the T-reg are by nature non proliferative). One such method can be performed using a whole animal system, e.g., loading cultured recipient APC's with peptides by either methods mentioned above, and reintroducing the cells into the same animal. Alternatively, donor peptides can be eluted from the recipient APC exposing Pep2Reg complexes and sequenced for identity.

Auxiliary Treatments

Methods of the invention can also include additional treatments, e.g., additional immunosuppressive treatments. For example, methods can include inactivating natural killer cells, preferably graft reactive or xenoreactive, e.g., swine reactive, NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the LRAPC's or a graft into the recipient mammal or prior to implanting the graft in the recipient. This antibody can be the same or different from an antibody used to inactivate cytotoxic T cells.

Methods include inactivating cytotoxic T cells, preferably graft reactive or xenoreactive, e.g., swine reactive, cytotoxic T cells of the recipient mammal. This can be accomplished, e.g., by introducing into the recipient mammal an antibody capable of binding to cytotoxic T cells of the recipient mammal. The administration of antibodies, or other treatment to inactivate cytotoxic T cells, can be given prior or concomitantly to introducing the LRAPC's into the recipient mammal. This antibody can be the same or different from an antibody used to inactivate natural killer cells.

Methods can include the administration of a short course of help reducing treatment, e.g., a drug or other chemical agent, which can induce graft acceptance to unmatched class I and/or minor antigens on the graft which is introduced into the recipient. The short course of help reducing treatment, e.g., a short course of high dose cyclosporine, or equivalent agent such as Tacrolimus (FK506), is generally administered at the time at the graft is introduced into the recipient. The duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times, the period required for a mature T cell of the recipient species to initiate rejection of an antigen after first being stimulated by the antigen.

Other embodiments include particularly where the graft includes hematopoietic cells, e.g., bone marrow hematopoietic cells can (optionally): the step of, prior to LRAPC's or donor graft transplantation, creating hematopoietic space, e.g., by irradiating the recipient mammal with low dose, e.g., less than 400, preferably less than 300, more preferably less than 200 or 100 rads, whole body irradiation to deplete or partially deplete the bone marrow of the recipient. As is discussed herein this treatment can be reduced or entirely eliminated.

Administration of LRAPC

The LRAPC's can be administered in a variety of ways, e.g., intravenously, intraperatoneally, intrathymicaly, intramuscularly.

The number of LRAPC's administered to the recipient can be increased by either or both of increasing the number of LRAPC's provided in a particular administration or by providing repeated administrations of LRAPC's.

Repeated LRAPC's administration can promote engraftment in graft recipients. Thus, the invention also includes methods in which multiple LRAPC administrations are provided to a recipient. Administrations can be given prior to, at the time of, or after graft implantation. In preferred embodiments multiple administrations of LRAPC's are provided prior to the implantation of a graft. Two, three, four, five, or more administrations can be provided. The period between administrations of LRAPC's can be varied. In preferred embodiments a subsequent administration of LRAPC's is provided: at least two days, one week, one month, or six months after the previous administration of LRAPC's; when the recipient begins to show signs of host lymphocyte response to donor antigen, as is needed to maintain acceptance to donor antigen.

One or more post graft-implantation-administrations of LRAPC's can also be provided to minimize or eliminate the need for other treatments, e.g., irradiation. Post graft administration of LRAPC's can provided: at least two days, one week, one month, or six months after the previous administration of LRAPC's; at least two days, one week, one month, six months, or at any time in the life span of the recipient after the implantation of the graft; when the recipient begins to show signs of rejection, e.g., as evidenced by a decline in function of the grafted organ, by a change in the host donor specific antibody response, or by a change in the host lymphocyte response to donor antigen, is needed to maintain graft acceptance or otherwise prolong the acceptance of a graft.

Autoimmune Diseases

The invention can be used to treat and/or diagnose a variety of immune disorders. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Other Embodiments

The methods described herein for promoting the acceptance of an allogeneic antigen or allogeneic graft can be used where, as between the donor and recipient, there is any degree of mismatch at MHC loci or other loci which influence graft rejection. Preferably, there is a mismatch at at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. In any of these combinations other loci which control recognition and rejection, e.g., minor antigen loci, can be matched or mismatched. As stated above, it is preferable that there is mismatch at least one locus. Mismatched at MHC class I means mismatched for one or more MHC class I loci, e.g., in the case of humans, mismatched at one or more of HLA-A, HLA-B, or HLA-C. Mismatched at MHC class II means mismatched at one or more MHC class II loci, e.g., in the case of humans, mismatched at one or more of a DP, a DP, a DQ, a DQ, a DR, or a DR.

The methods described herein for acceptance of an allogeneic antigen or allogeneic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

The methods of the invention are particularly useful for replacing a tissue or organ afflicted with a neoplastic disorder, particularly a disorder which is resistant to normal modes of therapy, e.g., chemotherapy or radiation therapy. Methods of the invention can be used for inducing graft acceptance to a graft, e.g., an allograft, e.g., an allograft from a donor which is mismatched at one or more class I loci, at one or more class II loci, or at one or more loci at each of class I and class II. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Methods of the invention can include recipient splenectomy.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

The administration of the agent can be initiated: when the recipient begins to show signs of rejection, e.g., as evidenced by a decline in function of the grafted organ, by a change in the host donor specific antibody response, or by a change in the host lymphocyte response to donor antigen; as is needed to maintain or otherwise prolong the acceptance of a graft.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less. The period will generally be at least about one week and preferably at least about two weeks in duration. In preferred embodiments the period is two or three weeks long.

Where the graft includes hematopoietic cells, the method can include providing donor specific factors which promote engraftment. Some of the methods referred to herein include the administration of LRAPC's to a recipient. It is known that administration of one or more cytokines, preferably a cytokine from the species from which the tissue is derived, can promote engraftment, or otherwise prolong acceptance of a graft. The use of such cytokines can reduce or eliminate the need for whole body irradiation. Thus, the invention also includes methods in which the recipient is administered one or more cytokine, e.g., a donor-species cytokine.

Although not wishing to be bound by theory, it may be that the cytokines, particularly donor species cytokines, promote the engraftment and/or function of donor cells or their progeny cells. Accordingly, any method referred to herein which includes hematopoietic grafts can further include the administration of a cytokine, e.g., SCF, IL-3, or GM-CSF. In preferred embodiments the cytokine one which is species specific in its interaction with target cells.

Administration of a cytokine can begin prior to, at, or after the implantation of a graft or the implantation of grafts.

The method can further include the step of administering a first or subsequent dose of a cytokine to the recipient: when the recipient begins to show signs of rejection, e.g., as evidenced by a decline in function of the grafted organ, by a change in the host donor specific antibody response, or by a change in the host lymphocyte response to donor antigen, as is needed to maintain or otherwise prolong the acceptance of a graft. Thus, method of the invention can be modified to include a further step of determining if a subject is in need of cytokine therapy and if so, administering a cytokine.

The period over which the cytokine(s) is administered (or the period over which clinically effective levels are maintained in the subject) can be long term, e.g., for six months of more or a year or more, or short term, e.g., for a year or less, more preferably six months or less, more preferably one month or less, and more preferably two weeks or less. The period will generally be at least about one week and preferably at least about two weeks in duration.

In preferred embodiments the recipient is a primate, e.g., a human, and the donor is from a different species, e.g., the donor is a pig and: pig SCF is administered; pig IL-3 is administered; a combination of pig SCF and pig IL-3 is administered; a pig specific hematopoiesis enhancing factor, e.g., pig GM-SCF, is administered, e.g., after the implantation of a graft, e.g., about a month after the implantation of a graft.

A particularly preferred embodiment combines a short course, e.g., about a month, of cyclosporine or a similar agent, a short course, e.g., about two weeks, of 15-deoxyspergualin or a similar agent, and a short course, e.g., about two weeks, of donor specific cytokines, e.g., SCF and IL-3.

It is to be understood that while the invention has been described in conjunction with the detailed description thereof, the foregoing description is intended to illustrate and not limit the scope of the invention, which is defined by the scope of the appended claims.

EXAMPLES

The invention is further described in the following examples, which do not limit the scope of the invention described in the claims.

Example 1 is inhibition of T cell proliferation. Example 2 is class II cDNA expression but not cell surface presentation of the heterodimer in class II-committed cells. Example 3 is the computer prediction of MHC class II peptides docking onto self class II grooves. Example 4 is the CD4+CD25+ T-reg increased blast number and activation marker (CTLA4) when primed with immature dendritic cells. Example 5 is T-reg increased proliferation when previously primed in vivo with autologous dendritic cells and then incubated with these dendritic cells.

Example 1

Antibody-Mediated Inhibition of Proliferation of T Cells From Class II-Engineered Animals As seen in FIG. 1, the transfer of donor-class II transgenes (Tg) to an animal did not affect the ability of the recipient to respond to the transferred class II proteins through either the direct or indirect pathways.

(1). Class II transgene introduced. (2). The direct pathway of antigen presentation was assessed with purified T cells from class II engineered animals tested against donor-type irradiated PBLs. The indirect pathway was tested on recipient T cells, supplemented with self APC and stimulated by donor-type irradiated T cells. (3). The combination of anti-DR and -DQ mAbs resulted in 90-100% inhibition in all cases. (4). Not detected. (5). Results from a naïve animal representative of 5 experiments.

Example 2

Expression of Transduced MHC Class II cDNAs in Class II-Committed Cells

As seen in FIG. 2, flow cytometry analysis of surface protein expression from pig DRA+B cDNAs transduced into human B cells via recombinant retroviruses revealed no membrane-bound pig DR signals whereas similar transduction conditions applied to non-class II-committed cells, such as human fibroblasts, led to a clear surface signal (FIG. 1A). Lack of surface expression of pig DR heterodimers on human B cells was not due to poor Tg transcription in this cell type since the overall level of proviral DR message was even higher in B cells than fibroblasts (FIG. 1B). A limiting supply of the class II chaperon invariant chain in B cells was also not a limiting factor to pig class II surface expression since transfection with higher copy numbers of pig class II resulted in low pig class II surface expression on human B cells (result not shown). Low copy number transduced APC, expressing their own surface class II molecules but not the transgenic class II, stimulated the proliferation of autologous T cells primed in vitro by naïve APC exhibiting surface transgenic products (FIG. 1C, green bar). Such proliferation was selectively blocked by antibodies to APC surface class II suggesting that retrovirus-derived class II chains were processed into peptides, some of which being presented on surface class II from transduced APC, (FIG. 2C).

Example 3

MHC Class II Peptides Docking Onto Self Class II Grooves

Figure 3:
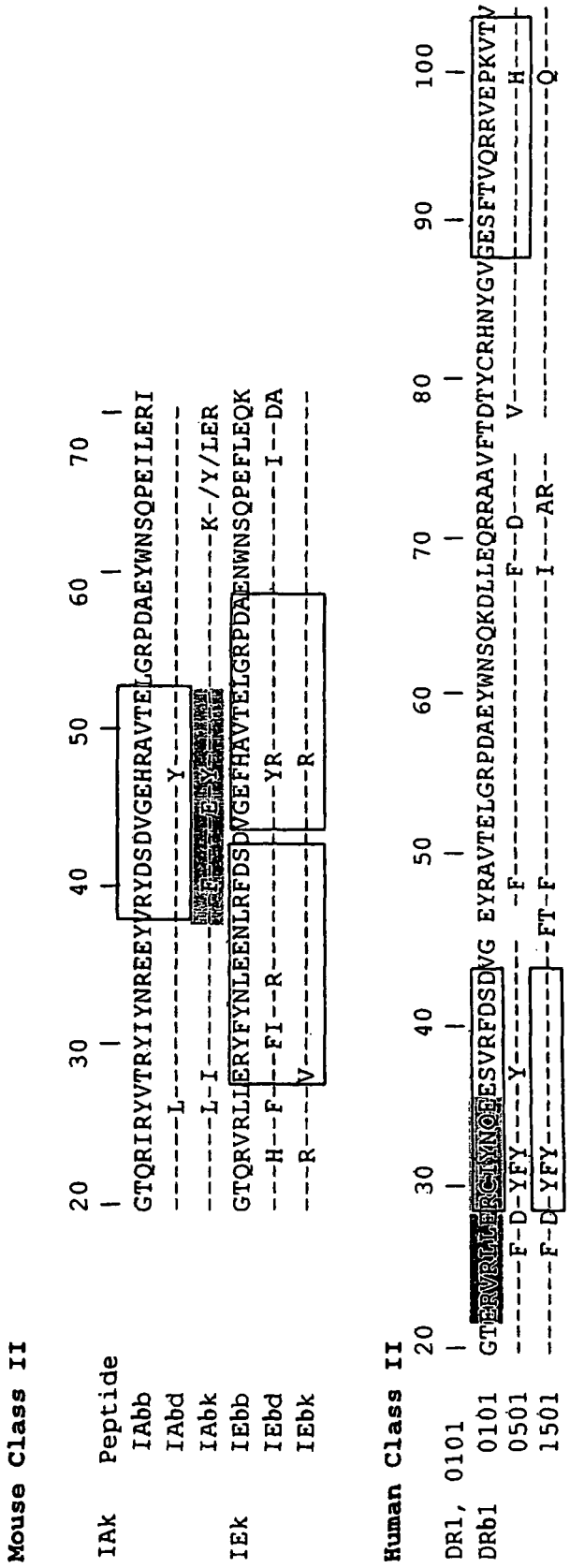
FIG. 3 is a diagram showing an alignment of MHC class II peptides, SEQ ID NOs 1-9 respectively, docking onto self class II grooves. Sequence predictions for 15-mer peptides fitting into autologous or allogeneic class II grooves were determined with the SYFPEITHI program. Boxes enclose peptide sequences with the highest fitting score. Shaded regions denote peptide sequences eluted from their autologous class II heterodimers. The limited information available on the crystal structure of the HLA-DQ molecules did not allow accurate design of potential DQ peptides to fit HLA-DQ grooves.

As seen in FIG. 3, computer predictions for potential high affinity class II peptide motifs docking into class II grooves identified mostly autologous Pep2Reg types, for example IA peptides binding preferentially into the IA groove. Furthermore, best fitted class II peptides preferentially derived from polymorphic regions between allelic b chains such as those from the murine IEb 27-57 and IAb 37-54 regions or human DRb1 22-44 (FIG. 3, boxes).

Example 4

Figure 4:
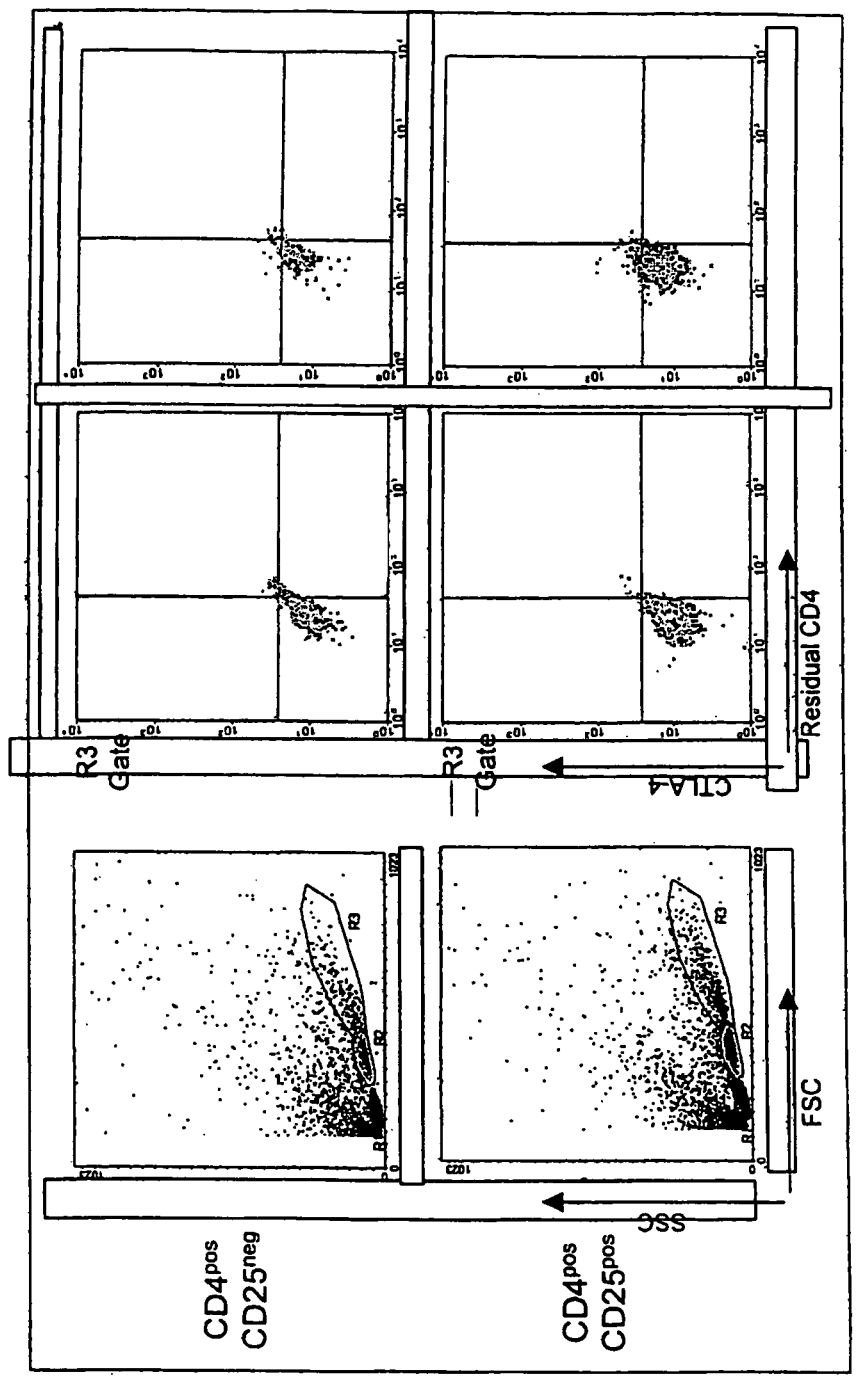
FIG. 4 is a flow cytometry diagram of CD4 positive subsets stimulated by autologous immature DC cells. Porcine T cells: Peripheral blood lymphocytes (PBL) from miniature swine were obtained by Ficoll-hypaque separation of heparanized whole blood as previously described (Thistlethwhite et al, Transplant. 35:394-400, 1983), depleted of monocytes and macrophages by plastic adherence overnight ($6 \times 10^6$ cells/ml of RPMI-1640 (Mediatech, Inc., Herndon, Va.) supplemented with 10% fetal calf serum (Sigma-Aldrich, St. Louis, Mo.), 1× non-essential amino acids (BioWhittaker, Inc., Walkersville, Md.), 1 mM sodium pyruvate (BioWhittaker, Inc., Walkersville, Md.), 10 mM HEPES (Mediatech, Inc., Herndon, Va.), 1× penicillin/streptomycin (BioWhittaker, Inc., Walkersville, Md.) and 25 ?M 2-mercaptoethanol) and of B cells by conventional nylon wool chromatography. CD4+ CD25+ and CD4+CD25− fractionated T cells were obtained by cell sorting (Cell Quest software, FACS Vantage SE, BD Immunocytometry Systems, San Jose, Calif.) after staining with a flourescein isothiocyanate-conjugated anti-porcine CD4 mAb (76-7-4) and a biotinylated anti-porcine CD25 mAb (K231.3B2) that was revealed with CyChrome-streptavidin. (BD Pharmingen, San Diego, Calif.). Porcine immature dendritic cells: Immature dendritic cells were obtained by culturing plastic adherent cells from PBL (detailed above) in 100 ng/ml porcine GM-CSF (BioTransplant, Charlestown, Mass.) and 10 ng/ml porcine IL-4 (BioSource International, Inc, Camarillo, Calif.) in RPMI medium (above) for 5 days. Fresh cytokines were added every other day. Non-adherent cells were then harvested and cultured at $2.5 \times 10^5$/ml in 6 well tissue culture plates (Costar; Corning, Inc., Acton, Mass.) for 2 additional days in fresh cytokines. On Day 7, adherent and non-adherent cells were harvested and used for co-culture studies. Co-culture of porcine T cells and iDC: $2 \times 10^5$ sorted T cells were incubated with $2 \times 10^4$ irradiated iDC (2500 rads) in a 200 ml total volume of MLR medium (RPMI-1640 supplemented as above except for 6% fetal pig serum rather than 10% fetal calf serum) per well of 96-well flat-bottomed plates (Costar; Corning, Inc., Acton, Mass.) for 7 days at 37° C. in 5-10% CO2. Flow cytometry analysis of T cells co-cultured with iDC: T cells were stained with a PE-conjugated anti-CTLA-4 (CD152) mAb (clone BN13, BD Pharmingen, San Diego, Calif.) per manufacturer's recommendations and analyzed using a FACScan II and CellQuest software (BD Immunocytometry Systems, San Jose, Calif.).

Flow Cytometry Analysis of CD4 Positive Subsets Stimulated by Autologous Immature DC Cells As seen in FIG. 4, results from studies performed in the miniature swine model show that: 1) CD4+, CD25+ T-reg-like cells produced more blasts than their CD4+, CD25neg counterpart following 1week priming in vitro with syngeneic iDC (CD1neg, CD2neg, CD3neg, Monocytepos, class IIpos), (FIG. 4, R3 gate); 2) T-reg-like cells also expressed marker of activation such as CTLA4 (FIG. 4, lower right panel).

Example 5

Stimulation of CD4+, CD25+ T Cells by Autologous Blood Cells

Figure 5:
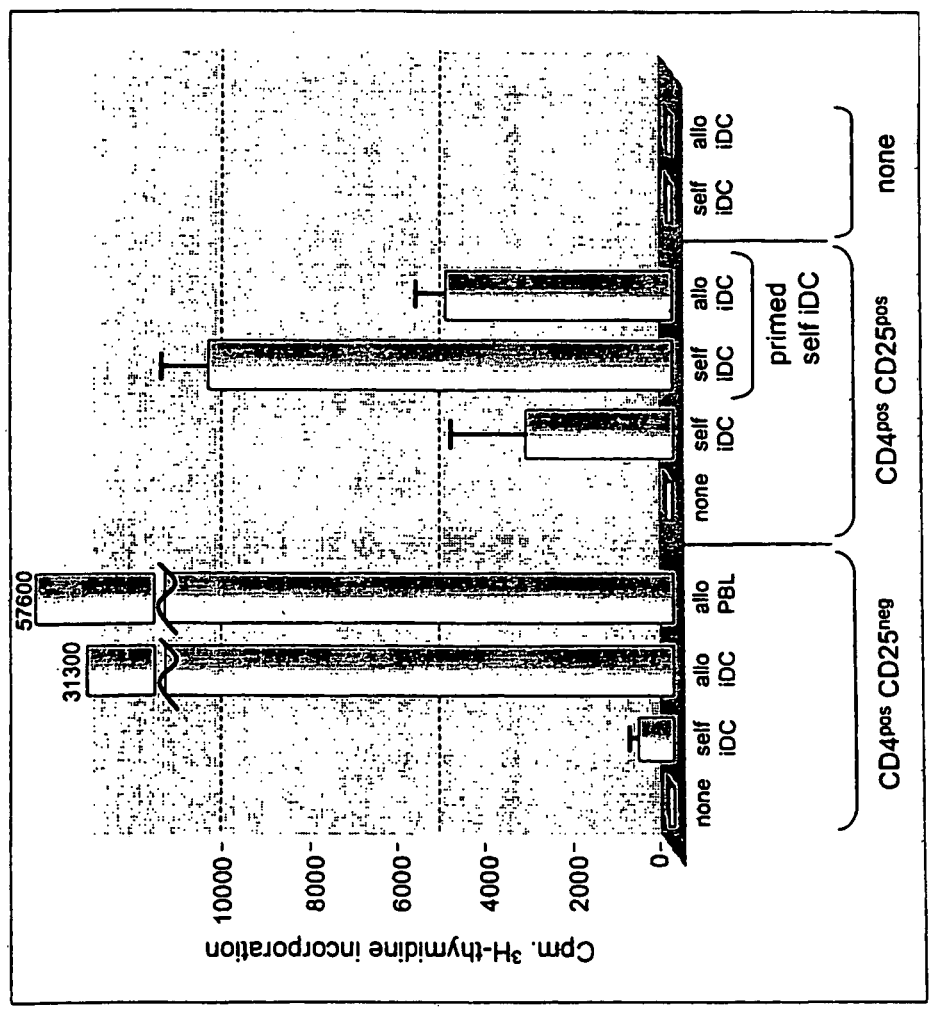
FIG. 5. is a graph illustrating stimulation of CD4+, CD25+ T cells by autologous blood cells. Peripheral blood lymphocytes (PBL) and iDC were prepared from the donor of T cells (self) or from an MHC allogeneic animal (allo). Irradiated PBL and iDC (2500 rads) were then used as stimulator cells in a 5 day proliferation assay involving either CD4+, CD25neg; CD4+, CD25+, or no (none) responders cells. After sorted T cells and irradiated iDC were co-cultured for 5 days (details above), the wells were pulsed with 2 µCi [3H]-thymidine per well for 24 hours. The plate was harvested and counted using a Tomtec Harvester and a Wallac Microbeta Counter (both from Perkin Elmer Life Sciences, Wellesley, Mass.). Results are expressed as the average±SD (3-5 wells) of 3H-thymidine incorporation after a 24 hour pulse. Similar data were obtained in 2 additional experiments.

As seen in FIG. 5, T cell activation by autologous iDC led to selective proliferation of the T-reg pool over the CD4+, CD25neg Th1-like subset. Proliferation of T-reg following incubation with autologous iDC was confirmed with T-reg previously primed in vitro with these dendritic cells.

What is claimed is:

1. A method of inhibiting allograft rejection in a subject in need thereof, the method comprising:
   providing antigen presenting cells (APCs) from the subject;
   loading a peptide fragment of an α or β chain of a preselected major histocompatibility complex (MHC) class II protein from the subject onto the subject's APCs outside the body of the subject, wherein the loading comprises introducing into the subject's APCs an expression vector encoding one or both of the α or β chain of the preselected MHC class II protein or synthesizing the peptide fragment and supplying the synthesized peptide fragment to the subject's APCs, and wherein the peptide fragment is presented on MHC class II proteins of the subject's APCs; and
   introducing the loaded APCs into the subject in an amount sufficient to activate autogenous peripheral T regulatory cells and suppress alloreactive autogenous cytotoxic T cells in the subject,
   thereby inhibiting allograft rejection in the subject.

2. The method of claim 1, further comprising evaluating the extent to which the subject's APC cells are loaded with the peptide fragment.

3. The method of claim 1, wherein the subject is human.

4. The method of claim 1, wherein the activated autogenous peripheral T regulatory cells include CD4+CD25+ cells.

5. The method of claim 1, wherein the loaded APCs are introduced into the subject intravenously.

6. The method of claim 1, wherein the loaded APCs are introduced into the subject intraperitoneally or intramuscularly.

7. The method of claim 1, wherein the loaded APCs are dendritic cells.

8. The method of claim 7, wherein the dendritic cells are immature dendritic cells.

9. The method of claim 7, wherein the dendritic cells are immature dendritic cells derived from bone marrow.

10. The method of claim 1, wherein the expression vector encodes the α chain of the preselected MHC class II protein.

11. The method of claim 1, wherein the expression vector encodes the β chain of the preselected MHC class II protein.

12. The method of claim 1, wherein the expression vector encodes the α and β chains of the preselected MHC class II protein.

13. The method of claim 1, wherein the loaded APCs are administered to the subject prior to allograft implantation into the subject.

14. The method of claim 1, wherein the loaded APCs are administered to the subject at the time of allograft implantation into the subject.

15. The method of claim 1, wherein the loaded APCs are administered to the subject after allograft implantation.

16. The method of claim 15, wherein the loaded APCs are administered to the subject at a single time point.

17. The method of claim 16, wherein the single time point is at least two days after the allograft implantation.

18. The method of claim 16, wherein the single time point is at least one week after the allograft implantation.

19. The method of claim 16, wherein the single time point is at least one month after the allograft implantation.

20. The method of claim 16, wherein the single time point is at least six months after the allograft implantation.

21. The method of claim 1, wherein the loaded APCs are administered to the subject when the subject begins to show signs of graft rejection.

22. The method of claim 21, wherein the signs of graft rejection are selected from the group consisting of: a decline in the function of a grafted organ, change in the subject's donor-specific antibody response, and a change in the subject's lymphocyte response to donor antigen.

23. The method of claim 1, wherein the allograft is an organ.

24. The method of claim 23, wherein the organ is a liver, kidney, heart, or lung.

25. The method of claim 1, wherein the allograft is selected from the group consisting of: bone or skeletal matrix, skin, intestine, and endocrine gland.

26. The method of claim 1, wherein the allograft is a musculocutaneous graft, a muscle flap, or hematopoietic cells.

27. The method of claim 1, wherein the allograft is a vascularized graft.

28. The method of claim 1, further comprising administering to the subject an agent selected from the group consisting of: cyclosporine, FK506, 15-deoxyspergualin, mycophenolate mofetil, and brequinar sodium.

29. The method of claim 1, further comprising the administration of a cytokine.

30. The method of claim 29, wherein the cytokine is a stem cell factor, interleukin-3, or granulocyte-macrophage colony-stimulating factor.

* * * * *